United States Patent
Kim et al.

(10) Patent No.: US 9,696,370 B2
(45) Date of Patent: Jul. 4, 2017

(54) PROBE STATION FOR THE SIMULTANEOUS MEASUREMENT OF THERMAL AND ELECTRICAL CHARACTERISTICS OF THERMOELECTRIC MODULE

(71) Applicant: KOREA UNIVERSITY RESEARCH AND BUSINESS FOUNDATION, Seoul (KR)

(72) Inventors: Sangsig Kim, Seoul (KR); Kyoungah Cho, Seoul (KR); Jinyong Choi, Seoul (KR); Jonggoo Lee, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 14/792,696

(22) Filed: Jul. 7, 2015

(65) Prior Publication Data
US 2016/0025801 A1    Jan. 28, 2016

(30) Foreign Application Priority Data
Jul. 25, 2014  (KR) .................. 10-2014-0094674

(51) Int. Cl.
*G01R 31/00* (2006.01)
*G01R 31/26* (2014.01)
(Continued)

(52) U.S. Cl.
CPC ........ *G01R 31/2601* (2013.01); *G01J 5/0096* (2013.01); *G01N 25/72* (2013.01); *G01J 2005/0077* (2013.01)

(58) Field of Classification Search
CPC ............ G01R 19/0092; G01R 31/2601; G01R 31/308; G01R 33/30; G01R 33/302;
(Continued)

(56) References Cited

U.S. PATENT DOCUMENTS

| | | | | |
|---|---|---|---|---|
| 6,111,421 A | * | 8/2000 | Takahashi | G01R 31/2868 324/750.04 |
| 2009/0224788 A1 | * | 9/2009 | Sasajima | G01R 31/2891 324/754.21 |

FOREIGN PATENT DOCUMENTS

| | | |
|---|---|---|
| JP | 2013-104667 A | 5/2013 |
| KR | 10-0485261 B1 | 4/2005 |
| WO | WO-2014/112215 A1 | 7/2014 |

OTHER PUBLICATIONS

Jinyong Choi, Kyoungah Cho and Sangsig Kim "Length-dependent thermoelectric characteristics of silicon nanowires on plastics in a relatively low temperature regime in ambient air", Nanotechnology, 24, published Oct. 18, 2013.

* cited by examiner

*Primary Examiner* — Vinh Nguyen
(74) *Attorney, Agent, or Firm* — Rabin & Berdo, P.C.

(57) ABSTRACT

Provided is a probe station system which can measure thermal distribution and thermographic images. More particularly, a probe station is provided which can detect an electrical characteristics change according to the supply of heat to an element, for example a thermoelectric element to measure the characteristics of the element. The probe station for the simultaneous measurement of thermal and electrical characteristics of a thermoelectric element includes: a chamber, a base, a platform, a probe unit, a heat source, and an infrared image detection unit and the thermographic image and the voltage signal of the element are synchronized in real time.

13 Claims, 9 Drawing Sheets

(51) Int. Cl.
*G01N 25/72* (2006.01)
*G01J 5/00* (2006.01)

(58) Field of Classification Search
CPC .. G01R 33/4804; G01R 33/54; G01R 31/045; G01N 25/72; G01N 27/72; G01N 15/0205; G01N 30/54; G01N 30/88; G01N 29/228; G01N 25/00; G01S 13/89; H04N 1/107; H04N 2201/0471; H04N 2201/04717; H04N 1/031; H04N 1/1075; H04N 5/2258; G01J 2005/0077; G01J 5/10; G01J 5/02; G01J 2005/0081; G01J 5/0896; G01M 3/002; G01M 3/04; G01M 3/38; G06F 9/06; G06T 2207/10024; G06T 7/0002

See application file for complete search history.

PROBE STATION FOR THE SIMULTANEOUS MEASUREMENT OF THERMAL AND ELECTRICAL CHARACTERISTICS OF THERMOELECTRIC MODULE

CROSS-REFERENCE TO RELATED APPLICATIONS

This application claims the benefit of Korean Patent Application No. 10-2014-0094674, filed on Jul. 25, 2014 in the Korean Intellectual Property Office, which is incorporated herein by reference in its entirety.

STATEMENT REGARDING PRIOR DISCLOSURES BY THE INVENTOR OR A JOINT INVENTOR

Applicant hereby states under 37 CFR 1.77(b) (6) that Jinyoung Choi, Kyoungah Cho and Sangsig Kim, Length-dependent thermoelectric characteristics of silicon nanowires on plastics in a relatively low temperature regime in ambient air, Nanotechnology 24, published 18 Oct. 2013, is designated as a grace period inventor disclosure. The disclosure: (1) was made one year or less before the effective filing date of the claimed invention; (2) names the inventor or a joint inventor as an author; and (3) does not name additional persons as authors on a printed publication.

BACKGROUND OF THE INVENTION

1. Field of the Invention

The present invention relate to a probe station system which can measure thermal distribution and thermographic images, and more particularly, to such an probe station which can detect an electrical characteristics change according to the supply of heat to an element, for example a thermoelectric element to measure the characteristics of the element.

2. Description of Related Art

Semiconductor devices are used in a wide range of industrial fields, and their application field expands gradually along with the innovation of semiconductor manufacture technologies and devices. In addition, a variety of applications meeting the trend toward more compactness and thinness are researched and manufactured.

A thermoelectric element of the semiconductor device uses the Seebeck effect. The thermoelectric element is an element in which a p- and n-doped semiconductor that is heated at one side thereof and is cooled at the other side thereof transports electric charges through an external circuit and performs electricity generation through a load. A traditional thermoelectric element was used as a simple functional element such as a thermocouple for measuring a temperature difference using the Seebeck effect and a constant temperature facility using the Peltier effect.

However, in recent years, the manufactures and researches taking the advanced structure are in active progress in a semiconductor device manufacture and material field along with the innovation of the semiconductor device manufacture technologies and devices. For example, the use of a nanowire or the like enables the manufacture of a more compact and flexible application in the manufacture of the thermoelectric element. A compact, high-performance thermoelectric element can implement a power generator as a wearable device.

Therefore, there is the need for rapid detection of whether or not the application is manufactured normally through the detection of the characteristics of the thermoelectric element or the thermoelectric element is operated normally. However, the conventional detection of the characteristics of the thermoelectric element in accordance with the prior art was performed by an indirect measurement method in which an electrical contact is achieved and a change in the electrical resistance of a metal line is measured and is converted into a temperature of the metal line. In other words, a conventional detection and measurement device includes a heat source disposed within a chamber, and a metal line and line that are disposed adjacent to the heat source. In this case, an object which is to be detected is disposed on the metal line and the signal line. Then, a temperature difference is caused to occur at both ends of the to-be-detected object through the heat source, and the electrode resistances of the manufactured to-be-detected object are measured through the metal line in the chamber that maintains a constant temperature for the measurement of a temperature of the to-be-detected object. The electrode resistances of the to-be-detected object vary depending on temperature, and thus the resistances of the electrodes of the to-be-detected object are measured individually by incrementing the temperature by 1K. A process is repeatedly performed which measures the electrode resistances of the to-be-detected object with the temperature incremented to increase accuracy and again measures the electrode resistances of the to-be-detected object according to the temperature with a staring temperature decremented. Because the relationship between temperature and resistance of the element shows a linear characteristics, the temperature of the electrodes at both ends of the to-be-detected object, i.e., the element such as the nanowire can be checked using measured resistance values collected from data gathered through this process, and the characteristics of the to-be-detected object, i.e., a Seebeck coefficient can be calculated by acquiring the temperature data converted from the measured resistance values and a voltage signal difference from the signal line. This process varies depending on elements, and thus a measurement needs to be performed by each element.

However, this method entails a problem in that because it is impossible to measure a voltage difference between both ends of the nanomaterial using a voltmeter and simultaneously measure the resistances of the electrodes at both ends of the nanomaterial together, the voltage difference and the temperature of both ends of the to-be-detected object cannot be measured. For this reason, the voltage difference between both ends of the to-be-detected object is first measured and then the resistances of the electrodes at both ends of the to-be-detected object are measured. This method causes a time difference between the detected results, and thus ultimately induces an error in the calculation of the characteristics of the to-be-detected object element. In particular, the measurement of temperature and voltage of the to-be-detected object in accordance with the prior art must be performed in a vacuum atmosphere and the measurement of temperature of the element must be performed in a low temperature environment. As such, a measurement environment condition is complicated as well as the measurement of temperature of an um unit under this environment is considerably difficult. Furthermore, the grasping itself of heat distribution is difficult, thus making it difficult to secure reliability of the measured values.

SUMMARY OF THE INVENTION

Accordingly, the present invention has been made to solve the above-mentioned problems involved in the conventional block matching apparatus, and it is an object of the present invention to provide a thermoelectric module detection device in which the temperature of a direct element can be measured directly using thermographic information and the entire heat distribution of the element can be grasped so as to solve a degradation of reliability involved in a conventional indirect measurement method implementing a temperature inversion process through the measurement of resistance of a direct electrical contact and a metal line, thereby reducing the process time and enabling the reliable detection.

To accomplish the above objects, the present invention provides a probe station for the simultaneous measurement of thermal and electrical characteristics of a thermoelectric element, including: a chamber including an inward receiving unit having a window, the inward receiving unit being configured to be seated inwardly of the chamber through a chamber cover opening formed on one surface thereof; a base disposed within the chamber; a platform disposed on the base and configured to allow the element to be disposed thereon so that a voltage of the element is detected, the platform being configured to allow a platform terminal for detecting a voltage signal of the element to be disposed thereon; a probe unit disposed at one end thereof within the chamber and including a probe tip that can be connected to the platform terminal; a heat source disposed within the chamber and configured to provide heat to the element so that the voltage signal of the element can be detected; and an infrared image detection unit at least partially disposed in the inward receiving unit so that a thermographic image of the element, which is generated by reaction due to heat provided from the heat source, can be acquired through the window, and wherein the thermographic image and the voltage signal of the element are synchronized in real time.

In the probe station for the simultaneous measurement of thermal and electrical characteristics of a thermoelectric element, the window may be a Ge window configured to allow an infrared ray to transmit therethrough.

In the probe station for the simultaneous measurement of thermal and electrical characteristics of a thermoelectric element, the platform may be disposed on the base and may include a platform plate for allowing the platform terminal to be disposed thereon, and the platform terminal may include: a terminal line configured to form a pair so as to be disposed opposed to each other on one surface of the platform plate, and configured to allow the element to be disposed between the pair of terminal lines; and a terminal tip disposed at an end of the terminal line and configured to allow the probe tip to be brought into close contact therewith.

In the probe station for the simultaneous measurement of thermal and electrical characteristics of a thermoelectric element, the heat source may be a joule heater disposed on the platform plate, and the heat source may include: a heater line disposed at the outside of the terminal line, which is disposed on one surface of the platform plate so that the element can be disposed on the terminal line; and a heater tip disposed at and end of the heater line and configured to allow an electrical signal to be applied thereto.

In the probe station for the simultaneous measurement of thermal and electrical characteristics of a thermoelectric element, the heat source may form a pair so as to be disposed opposed to each other relative to the center of the terminal line so that heat can be outputted individually.

The probe station for the simultaneous measurement of thermal and electrical characteristics of a thermoelectric element may further include: a storage unit for storing the thermographic image and the electrical characteristics of the element in response to a storage control signal, and pre-stored temperature reference data that enables a temperature state of the thermographic image to be grasped; a control unit for in real time, synchronizing the thermographic image and the voltage signal of the element, which are previously stored in the storage unit, and calculating a heat temperature difference occurring at both ends of the element based on the thermographic image and the pre-stored temperature reference data; and an arithmetic unit for calculating the characteristics of the element in response to an arithmetic control signal from the control unit based on the heat temperature difference and the voltage signal of both ends of the element.

In the probe station for the simultaneous measurement of thermal and electrical characteristics of a thermoelectric element, the inward receiving unit may include: an inward receiving body fixedly mounted in the chamber cover opening; an inward receiving plate disposed spaced apart from the inward receiving body and configured to be movable toward the inside of the chamber, with the window formed in the inward receiving plate; and an inward receiving bellows connected at one end thereof to the inward receiving body and connected at the other end thereof to the inward receiving plate so that the inward receiving bellows can be folded depending on the position of the inward receiving plate.

The probe station for the simultaneous measurement of thermal and electrical characteristics of a thermoelectric element may further include a receiving unit guide connected at one end thereof to the inward receiving plate through the inward receiving body and disposed at the other end thereof at the outside of the chamber to allow the receiving unit guide to be adjusted in length through the other end of the receiving unit guide so that the inward receiving plate is adjusted in position.

In the probe station for the simultaneous measurement of thermal and electrical characteristics of a thermoelectric element, the image detection unit may include: an image detection sensor for acquiring a thermographic image of the element through the window; and an image detection holding part for allowing the image detection sensor to be maintained at the outside of the chamber.

In the probe station for the simultaneous measurement of thermal and electrical characteristics of a thermoelectric element, the mage detection holding part may include: a detection holder disposed so as to be connected to an end of the image detection sensor; a detection holder around formed extending radially outwardly from an outer circumferential surface of the detection holder; and a detection holder housing disposed at the outside of the detection holder around to enable the longitudinal relative displacement between the detection holder housing and detection holder around.

In the probe station for the simultaneous measurement of thermal and electrical characteristics of a thermoelectric element, the detection holder around may include a holder around guide 524 formed on the outer peripheral surface thereof, and the detection holder housing may include a holder housing guide formed on the inner peripheral surface thereof so as to be engaged with the holder around guide to enable the relative movement between the holder housing guide and the holder around guide.

In the probe station for the simultaneous measurement of thermal and electrical characteristics of a thermoelectric element, the detection holder around may include a through-hole formed therein, and wherein the detection holder housing may include a holder housing shaft disposed penetratingly in the through-hole of the detection holder around so that the image detection sensor can be moved longitudinally.

In the probe station for the simultaneous measurement of thermal and electrical characteristics of a thermoelectric element, the image detection unit may include an image detection driving unit configured to drive the image detection holding part to provide a driving force for displacing the image detection sensor to the detection holder, and the image detection drive unit may include: a detection driver for generating the driving force for displacing the image detection sensor; and a detection drive transfer unit connected at one end thereof to the detection driver and connected at the other end thereof to the detection holder to transfer the driving force generated from the detection driver to the detection holder.

Effects of the Invention

According to the probe station for the simultaneous measurement of thermal and electrical characteristics of a thermoelectric element of the present invention, the thermal distribution and temperature can be directly detected by excluding the temperature conversion according to a resistance of a metal and using the image detection sensor that is implemented as an infrared camera, and simultaneously the voltage signal as the electrical characteristics of the element can be measured, thereby reducing the entire process time and thus decreasing the process cost.

According to the probe station for the simultaneous measurement of thermal and electrical characteristics of a thermoelectric element of the present invention, the arrangement structure of the inward receiving unit seated inwardly of the chamber and the arrangement of the image detection sensor of the image detection unit in the inward receiving unit enable thermographic information on the element be acquired at a position which is nearer to the element.

According to the probe station for the simultaneous measurement of thermal and electrical characteristics of a thermoelectric element of the present invention, the movement structure of the image detection sensor enables the change of the focusing position of the image detection sensor depending on the size of the element to allow for the accurate acquisition of the thermographic information of the element so that the characteristics of the element such as the Seebeck coefficient can be more accurately analyzed through synchronization with the measured voltage signal.

According to the probe station for the simultaneous measurement of thermal and electrical characteristics of a thermoelectric element of the present invention, the use of the thermographic information acquired by the image detection sensor of the image detection unit enables the thermal distribution of the element to be acquired so that a local deterioration phenomenon of a nanoelectronic device can be detected.

In addition, according to the probe station for the simultaneous measurement of thermal and electrical characteristics of a thermoelectric element of the present invention, the temperature of a thermoelectric element detected is converted into a wavelength so that various characteristics of the element can be analyzed.

BRIEF DESCRIPTION OF THE DRAWINGS

The above and other objects, features and advantages of the present invention will be apparent from the following detailed description of the preferred exemplary embodiments of the invention in conjunction with the accompanying drawings, in which.

EXPLANATION ON SYMBOLS

10: probe station for the simultaneous measurement of thermal and electrical characteristics of a thermoelectric element
20: control unit
30: storage unit
40: arithmetic unit
100: chamber 200: base
300: platform
400: probe unit
500: image detection unit

DESCRIPTION OF THE PREFERRED EMBODIMENTS

Now, preferred embodiments of the present invention will be described hereinafter in detail with reference to the accompanying drawings. It should be noted that the same elements in the drawings are denoted by the same reference numerals although shown in different figures. In the following description, the detailed description on known function and constructions unnecessarily obscuring the subject matter of the present invention will be avoided hereinafter.

Figure 1:
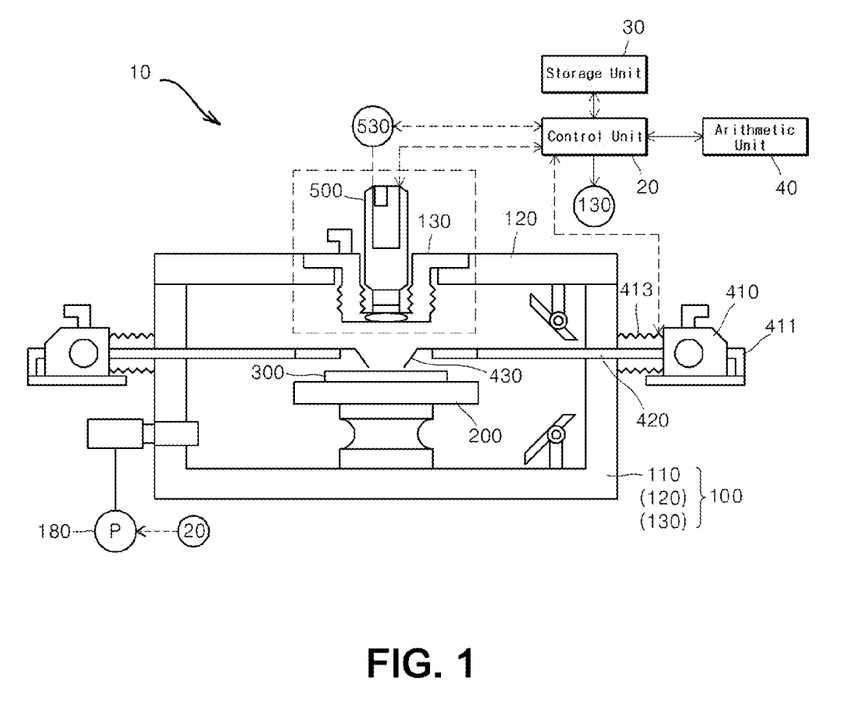
FIG. 1 is a schematic block diagram showing a configuration of a probe station for the simultaneous measurement of thermal and electrical characteristics of a thermoelectric element in accordance with an embodiment of the present invention.

A probe station 10 for the simultaneous measurement of thermal and electrical characteristics of a thermoelectric module in accordance with an embodiment of the present invention includes a chamber 100, a base 200, a platform 300, a probe unit 400, a heat source 600, and an image detection unit 500. The probe station 10 for the simultaneous measurement of thermal and electrical characteristics of a thermoelectric module has a structure in which a thermographic image and a voltage signal as the electrical characteristics of the thermoelectric element which it is desired to detect are simultaneously measured in real time to enable synchronization.

The chamber 100 includes an inward receiving unit 130 having a window and configured to be seated inwardly through a chamber cover opening 121 formed on one surface thereof. More specifically, the chamber 100 includes a chamber body 110 and a chamber cover 120. The chamber body 110 and the chamber cover 120 are engaged with each other to define an internal space therebetween. A constituent element may be disposed at a side of the chamber body 110 to form an atmosphere within the chamber 100. A chamber atmosphere regulation unit 410 may be disposed through a chamber connection member formed at a side of the chamber body 110. The chamber atmosphere regulation unit 140 can be implemented as a compressor or a pump. In other words, a vacuum atmosphere may be formed in the chamber through the operation of the chamber atmosphere regulation unit 140. On the contrary, the probe station may be configured in various manners such as regulating the internal atmosphere of the chamber as a specific gas atmosphere in such a manner as to inject a predetermined atmosphere gas such as nitrogen into the chamber.

The chamber cover 120 is disposed on an upper end of the chamber body 110. The chamber cover 120 is engaged with the chamber body 110 to have a given internal space defined therebetween. The inward receiving unit 130 is mounted on one surface of the chamber cover 120. In other words, the inward receiving unit 130 is seated in the chamber cover opening 121 formed on one surface of the chamber cover 120. A seating part 123 and a stepped part 125 are formed on the outer peripheral portion of the chamber cover opening 121. The seating part 123 has a structure in which the inward receiving unit 130 is partially seated on the seating part 123. The stepped part 125 is brought into close contact with the outer peripheral end of the inward receiving unit 130 so that the inward receiving unit can be prevented from escaping from the chamber cover 120.

The base 200 is disposed in the internal space defined in the chamber 100. In this embodiment, the base 200 is fixedly disposed within the chamber 100, but may include a separate base drive unit (not shown) to have a structure in which a stage is moved on a predetermined coordinate axis.

Figure 2:
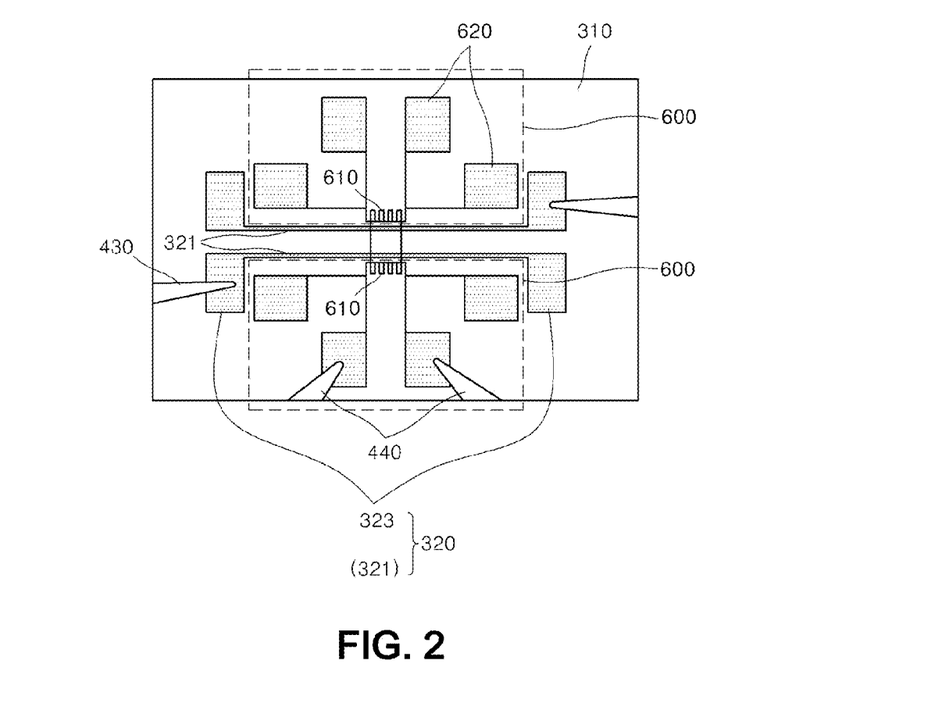
FIG. 2 is a partial top plan view schematically showing a configuration of a platform of a probe station for the simultaneous measurement of thermal and electrical characteristics of a thermoelectric element in accordance with an embodiment of the present invention.
Figure 3:
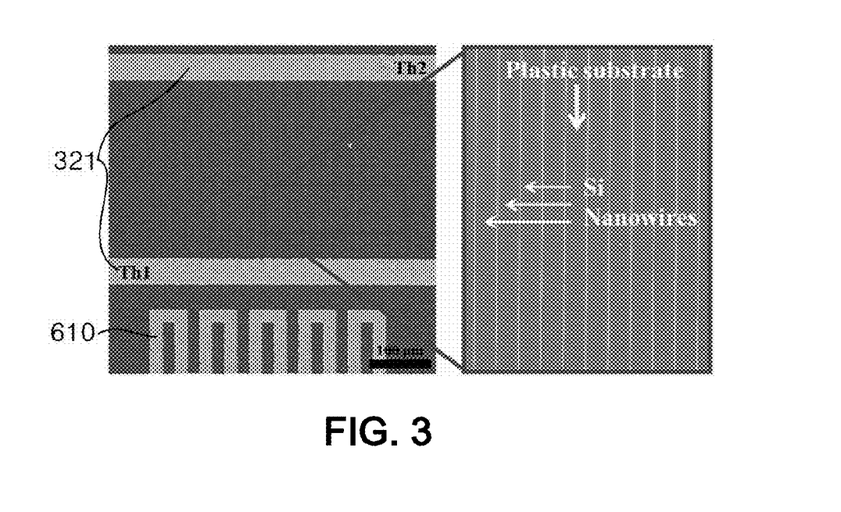
FIG. 3 is a partial enlarged top plan view schematic showing a configuration of a platform of a probe station for the simultaneous measurement of thermal and electrical characteristics of a thermoelectric element in accordance with an embodiment of the present invention.

The platform 300 is disposed on the base 200 and allows an element (not shown) which is to be detected to be disposed on one surface thereof. That is, disposed on the platform is a nanowire used as a thermoelectric element for detecting a voltage, a thermoelectric module used as a unit module, or an element for detecting the characteristics which is to be calculated through the Seebeck effect. As shown in FIG. 2, the platform 300 includes a platform plate 310 and a platform terminal 320. The element can have a structure in which it is stably seated on one surface of the platform plate 310. The platform terminal 320 for detecting a voltage signal of the element is disposed on one surface of the platform plate 310 so that the voltage signal as the electrical characteristics of the element seated on one surface of the platform plate 310 can be detected. In this embodiment, the platform terminal 320 includes a terminal line 321 and a terminal tip 323, which are formed on surface of the platform plate 310. The terminal line 321 has a structure in which it forms a pair so as to be disposed opposed to each other on one surface of the platform plate 310 and the element is disposed between the pair of the terminal lines 321. In other words, the terminal line 321 has a structure in which a pair of terminal lines are disposed opposed to each other so as to be spaced apart from each other at predetermined intervals so that elements such as nanowires as thermoelectric elements or a thermoelectric module consisting of the thermoelectric elements can be disposed between the pair of terminal lines. In FIGS. 2 and 3, there is shown a thermoelectric module including a plurality of nanowires as thermoelectric elements, i.e., elements as to-be-detected objects disposed on the terminal line 321. Herein, the plurality of nanowires is disposed on a substrate, for example, a flexible transparent substrate such that the nanowires are in close contact with the terminal line to enable the measurement of a voltage signal of the nanowires. In other words, a voltage applied to both ends of the element as a to-be-detected object is measured. The measured voltage can be calculated as a voltage difference occurring at both ends of the element through a subsequent detection process so as to be used to derive the characteristics of the element.

Although it has been illustrated in this embodiment that the terminal line 321 is formed in a linear shape in which a pair of terminal lines is disposed in parallel with each other, this is merely illustrative and the platform terminal line can be implemented in various manners within a range of enabling the measurement of a voltage of the disposed element, such as having a structure in which the terminal line has various intervals depending on a gap between the elements.

The terminal tip 323 is disposed at an end of the terminal line 321 on which the element is contactingly disposed, and can transfer a voltage output signal to an external device of the chamber such as a control unit through the contact between the terminal tip 323 and a probe tip 430 of a probe unit 400 which will be described later. The terminal tip 323 has a structure in which terminal tips are connectingly disposed at an end of each terminal line 321. The terminal tip 323 may be modified in various manners such as having a structure in which a plurality of terminal tips is connectingly disposed on each terminal line 321.

The probe station 10 for the simultaneous measurement of thermal and electrical characteristics of a thermoelectric module in accordance with the present invention includes a heat source 600 that provides heat to a thermoelectric element. The heat source 600 is disposed within the chamber and provides heat to one side of the element so that a voltage signal generated from the element through the Seebeck effect can be measured. The heat source 600 may use a laser source having various wavelengths or a heater for providing a mechanical heat. In this embodiment, the heat source 600 uses a joule heater based on a metal line. The heat source 600 used as the joule heater is disposed on the platform plate 310. The heat source 600 includes a heater line 610 and a heater tip 620. The heater line 610 is disposed at the outside of the terminal line 321 of the platform terminal 320, which is disposed on one surface of the platform plate 310 so that the element can be disposed on the terminal line. The heater tip 620 is disposed at an end of the heater line 610 and allows an electrical signal to be applied thereto. In other words, the external terminal (e.g., a tip 440 shown in FIG. 2) is brought into close contact with the heater tip 620 to apply an electrical signal to the heater tip 620, and heat is generated from the heater line 610 connected to the heater tip 620 due to resistance so that heat is provided to the element disposed on the terminal line 321 of the platform terminal 320.

The disposition of the heater line 610 can be implemented in various manners depending on a design specification but the heater line 610 has a structure of forming a pair. In other words, the heater line 610 of the heat source 600 has a structure in which it forms a pair so as to be disposed opposed to each other relative to the center of the terminal line 321 so that heat can be outputted individually. The disposition of the heater is preferable in that a test of the element characteristics can be performed under various environments.

The image detection unit 500, more specifically, an image detection sensor 510 of the image detection unit 500 is at least partially disposed in the inward receiving unit 130 so that a thermographic image of the thermoelectric element or the thermoelectric module, which is generated by reaction due to heat provided from the heat source, can be acquired through a window 137. The image detection sensor 510 that acquires the thermographic image is implemented as an infrared camera.

Figure 4:
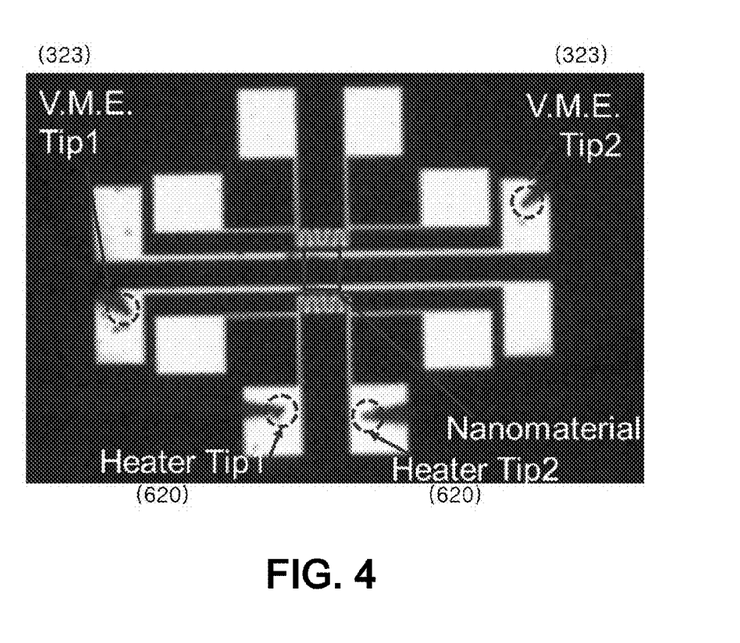
FIG. 4 is a schematic view showing a thermographic image of a platform of a probe station for the simultaneous measurement of thermal and electrical characteristics of a thermoelectric element in accordance with an embodiment of the present invention.

FIG. 4 shows thermographic information acquired through the image detection sensor 510 of the image detection unit 500, which will be described later, with respect to the platform 400 and the heat source 600. The heat source 600 causes a temperature difference to occur at both ends of the element, i.e., the thermoelectric element or the thermoelectric module, and at the same time, the element characteristics such as a Seebeck coefficient S of the thermoelectric element or the thermoelectric module can be calculated using the thermographic information of a corresponding element and a voltage difference occurring at both ends of the element from a voltage signal calculated through the platform terminal 320.

FIGS. 5 to 9 show a process of acquiring a thermographic image of an element and a voltage signal outputted as an electrical signal, which can be acquired simultaneously according to the present invention.

Figure 5:
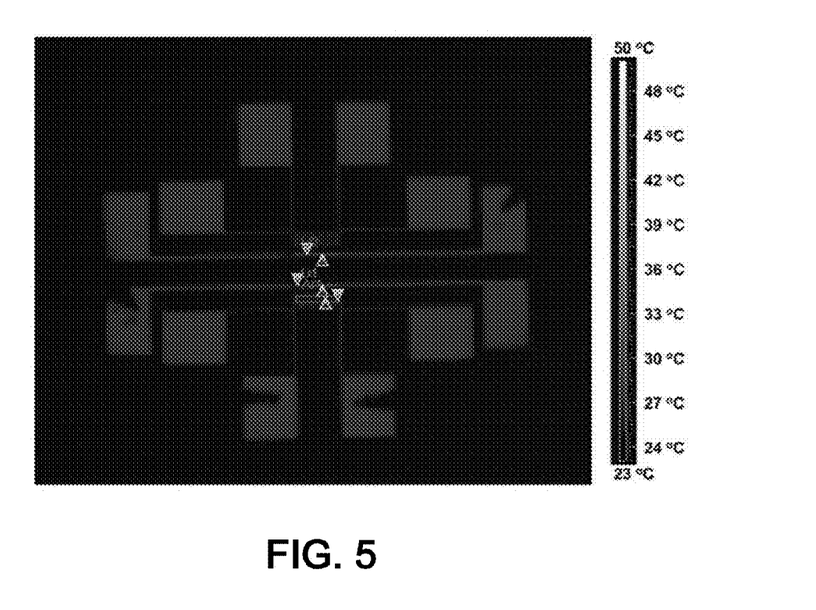
FIGS. 5 to 9 are views showing a configuration of a thermographic information image in a thermoelectric element characteristics detection process through a probe station for the simultaneous measurement of thermal and electrical characteristics of a thermoelectric element in accordance with an embodiment of the present invention.
Figure 6:
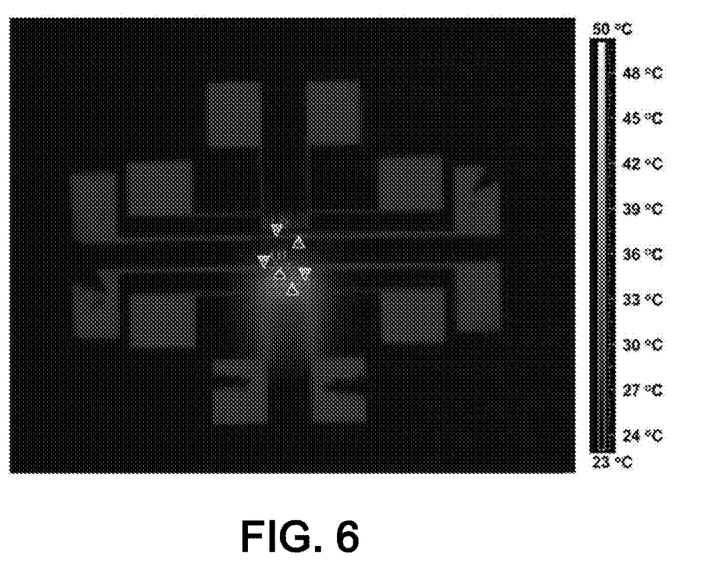
Figure 7:
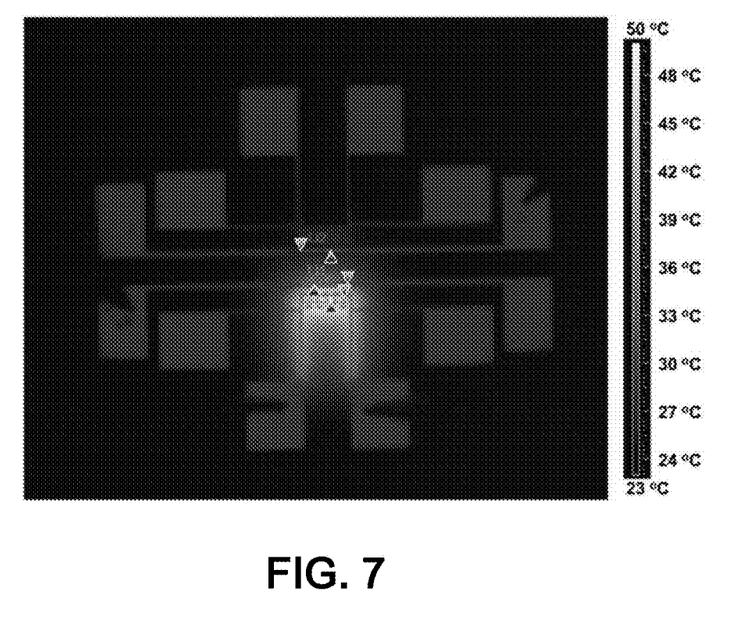
Figure 8:
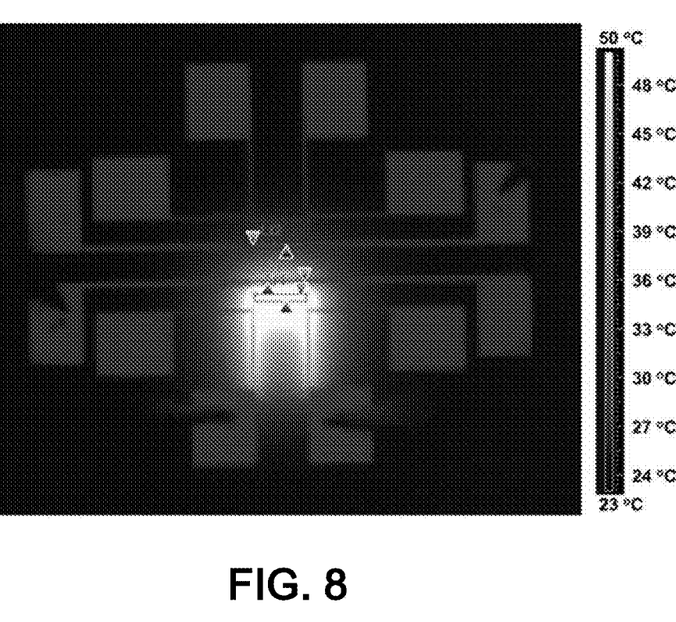
Figure 9:
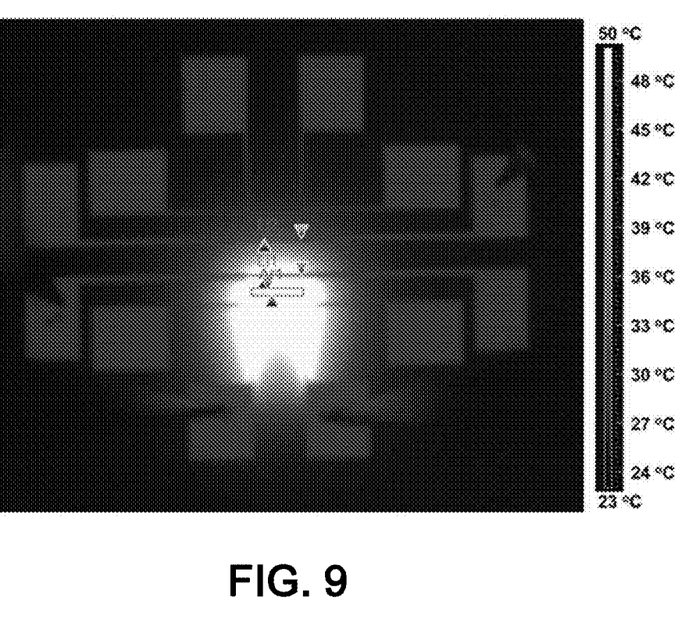
Figure 10:
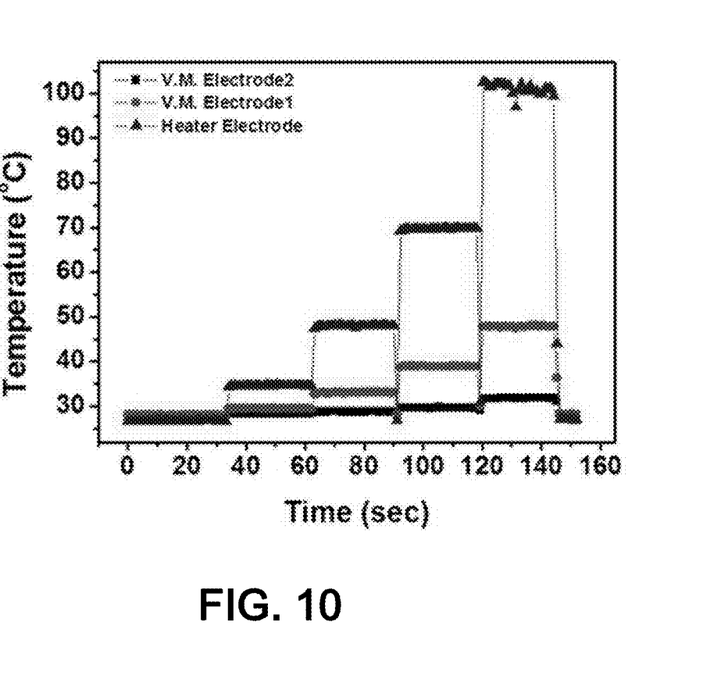
FIG. 10 is a diagrammatic view showing the temperature and electrical characteristics in the process shown in FIGS. 5 to 9.

First, as shown in FIG. 5, a sample which is to be detected is disposed on the platform 300. The element may be an individual thermoelectric element such as a nanowire or a thermoelectric module as a unit body. Like this, the element can be selected and applied in various manners.

Thereafter, a signal is applied to the heat source 600 to cause a heat transfer phenomenon to occur in a certain heat source 600. In this case, the heat source 600 which is implemented as a joule heater continuously rises up to a predetermined heat temperature and performs a heat transfer function as shown in FIGS. 6 to 9. In this embodiment, the heat transfer function was performed in such a manner as to increase the temperature of the heat source 600 by a constant time period. There are shown a heat temperature (or a temperature difference) at both ends of the element at the heat source 600 side and a voltage signal (or a voltage difference) detected at the terminal tip 323 connected to the terminal line 321 at each time period. It can be seen that a relatively linear relationship is formed between the temperature difference and the voltage difference at each time period, and a predetermined Seebeck coefficient for the element can be calculated using the temperature difference and the voltage difference. Herein, although the heat source 600 has a structure in which the heater line form a symmetrical arrangement to perform a heat transfer function at one end only, measurement or verification can be carried out in various manners, such as performing the heat transfer function at both ends.

Meanwhile, the probe station 10 for the simultaneous measurement of thermal and electrical characteristics of a thermoelectric module in accordance with the present invention may include a storage unit 30, a control unit 20, and an arithmetic unit 40. The storage unit 30 can store the thermographic image and the electrical characteristics of the element and can be operated in response to a storage control signal from the control unit 20. The control unit 20 can, in real time, synchronize the thermographic image and the voltage signal of the element, which are previously stored in the storage unit 30, and can calculate a heat temperature difference occurring at both ends of the element based on the thermographic image and the pre-stored temperature reference data. The arithmetic unit 40 can calculate the characteristics of the element in response to an arithmetic control signal from the control unit 20 based on the heat temperature difference and the voltage signal of both ends of the element. In other words, the control unit 20 controls a detection signal detected by and outputted from the image detection unit 500, i.e., thermographic information on the element to be stored in the storage unit 300, and calculates a heat temperature difference ($\Delta T = T_h - T_c$) for a corresponding element based on the temperature reference data which is previously stored in the storage unit 30 and the detection signal as the thermographic information on the element. The characteristics of the element as a to-be-detected object, i.e., a parameter S indicating the Seebeck effect can be calculated as follows by the arithmetic unit 40 based on a voltage signal detected from the terminal line 321 and the terminal tip 323, i.e., a voltage difference Voc and the heat temperature difference ($\Delta T = T_h - T_c$) for the corresponding element:

$$S = \frac{\Delta V}{\Delta T} = \frac{V_s}{\Delta T} = \frac{V_s}{(T_h - T_c)}.$$

That is, the characteristics of the element, i.e., the Seebeck coefficient S is calculated in real time using the thermographic information on the element and the voltage signal, which are measured simultaneously so that the characteristics of the thermoelectric element for a corresponding material can be analyzed.

Figure 11:
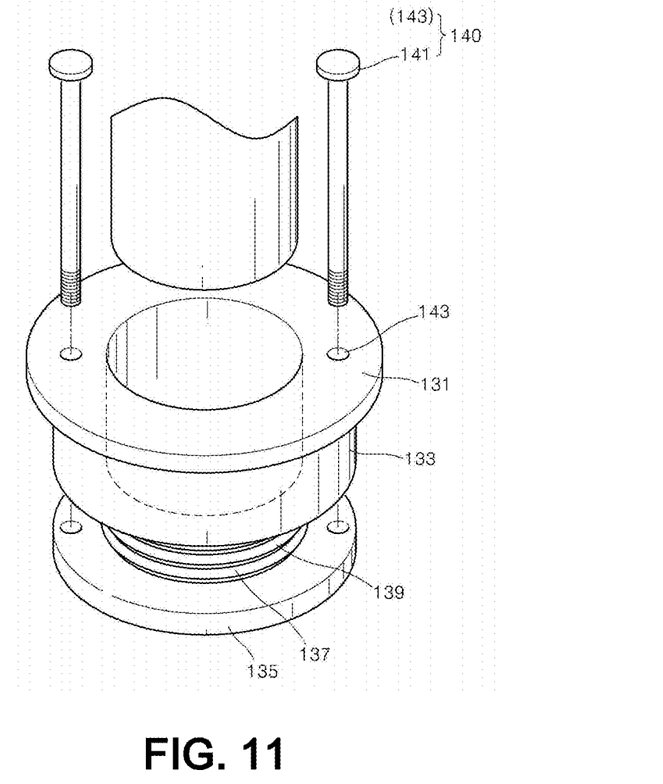
FIG. 11 is a schematic partial exploded perspective view showing an inward receiving unit of a probe station for the simultaneous measurement of thermal and electrical characteristics of a thermoelectric element in accordance with an embodiment of the present invention.
Figure 12:
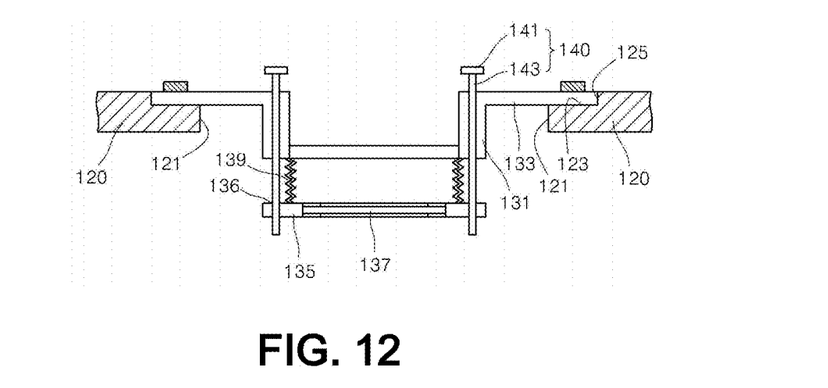
FIG. 12 is a cross-sectional view showing a mounting state of an inward receiving unit of a probe station for the simultaneous measurement of thermal and electrical characteristics of a thermoelectric element in accordance with an embodiment of the present invention.

In the meantime, the receiving space is defined in the chamber cover 120 of the chamber 100 by the chamber cover opening 121, and the inward receiving unit 130 is mounted in the chamber cover opening 121. The inward receiving unit 130 includes an inward receiving body 131; 133, an inward receiving plate 135, and an inward receiving bellows 139. The inward receiving body 131;133 is fixedly mounted in the chamber cover opening 121, and includes a radial extending part 131 and a vertical extending part 133. The radial extending part 131 and the vertical extending part 133 are integrally connected with each other. The radial extending part 131 has a structure in which it is formed extending radially outwardly from the center of the inward receiving unit 130 in parallel with the ground surface in the drawing and a through-hole is formed in the center thereof. The vertical extending part 133 has a structure in which it extends downwardly from the through-hole formed in the center of the radial extending part 131 so as to be oriented toward the inside of the chamber 100. The radial extending part 131 is at least partially seated on the seating part 123 formed on the outer peripheral portion of the chamber cover opening 121, and the outer peripheral end of the radial extending part 131 is engaged with the stepped part 125 of the chamber cover 120. The radial extending part 131 can be fixedly mounted to the chamber cover 120 by means of a separate fastening member, and a separate sealing member may further be provided between the radial extending part 131 and the seating part 123 or the stepped part 125 in order to ensure air-tightness therebetween.

The inward receiving plate 135 is disposed below the vertical extending part 133 and includes the window 137 disposed therein so as to allow a thermographic image of the element to be detected by the image detection unit 500 therethrough. In the present invention, the window 137 uses a germanium (Ge) window to allow light of an infrared wavelength ranging from 7-14 μm to transmit therethrough so that a thermographic image of an infrared wavelength can be detected. In other words, the Ge window 137 allows a predetermined infrared ray to transmit therethrough. A cutoff filter may be further provided at the inward receiving plate 135 so as to cut off light having an unwanted wavelength band of an ultraviolet (UV) ray or a visible ray, if necessary. In this embodiment, although the Ge window was used as the window, this is merely illustrative and is not limited thereto but the window can be modified in various manners such as being provided with a window allowing an infrared ray to transmit therethrough and formed of a material selected from the group consisting of germanium, calcium fluoride, and a compound thereof.

In addition, the inward receiving plate 135 is formed separately from the inward receiving body 131; 133. The reason for this is that there is a possibility that the position variation of the inward receiving plate 135 will be required to perform a focusing of the image detection unit 500 depending on the size of an element which is to be detected, if necessary. Thus, the inward receiving plate 135 may have a structure in which it can be displaced relative to the inward receiving body. In this case, the inward receiving bellows 139 can be connected to both ends of the inward receiving plate 135 and the inward receiving body 131; 133, which are formed separately from each other so that the inside of the chamber 100 can be maintained in a tightly sealed state. In other words, the inward receiving bellows 139 is connected at one end thereof to the inward receiving body 131; 133 and is connected at the other end thereof to the inward receiving plate 135 so that the inward receiving bellows can be folded depending on the position of the inward receiving plate 135.

In the meantime, a constituent element may be provided to ensure a stable relative position between the inward receiving plate 135 and the inward receiving body 131; 133. That is, the probe station 10 for the simultaneous measurement of thermal and electrical characteristics of a thermoelectric module in accordance with the present invention may further include a receiving unit guide 140. The receiving unit guide 140 includes a guide shaft 141, a body through-hole 143, and a plate through-hole 145. The guide shaft 141 is a fastening means such as a rectangular bolt. The body through-hole 143 denotes a through-hole longitudinally formed in the vertical extending part 133, and the plate through-hole 145 denotes a through-hole formed in the inward receiving plate 135 to correspond to the body through-hole 143. The receiving unit guide 140 is provided in plural numbers so as to be symmetrical with each other so that the inward receiving plate can be maintained in a more stable and horizontal state. The guide shaft 141 is at least passed at one end thereof through the body through-hole 143 and the plate through-hole 145 which has a corresponding fastening element, for example, a screw thread formed therein, to allow the guide shaft 141 to be adjusted in length through the other end of the guide shaft 141, which is disposed at the outside of the chamber, so that the inward receiving plate can be adjusted in position within the chamber 100.

Figure 13:
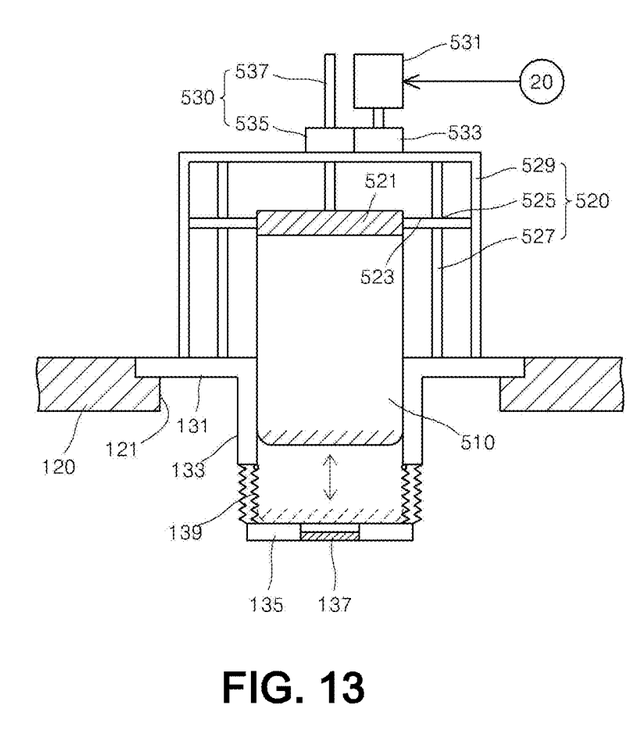
FIG. 13 is a schematic side cross-sectional view showing an image detection drive unit of a probe station for the simultaneous measurement of thermal and electrical characteristics of a thermoelectric element in accordance with another embodiment of the present invention.

Also, meanwhile, the present invention may be configured such that the image detection sensor of the image detection unit is adjusted in position unlike a configuration in which the inward receiving plate of the inward receiving unit is adjusted in position. In other words, the image detection unit 500 includes an image detection sensor 510 and an image detection holding part 520. The image detection sensor 510 is implemented as an infrared camera and acquires a thermographic image of the element through the window 137. The image detection holding part 520 allows the image detection sensor 510 to be maintained at the outside of the chamber 100. The image detection holding part 520 includes a detection holder 521, and a detection holder around 523, and a detection holder housing 529. The detection holder 521 is disposed so as to be connected to an end of the image detection sensor 510. The detection holder 521 is connected to the end of the image detection sensor 510 so that the image detection sensor 510 can secure a stable position at an upper portion of the chamber cover 120 and an upper portion of the inward receiving unit 130. The detection holder around 523 is formed extending radially outwardly from an outer circumferential surface of the detection holder 521. The detection holder housing 529 is disposed at the outside of the detection holder around 523 to enable the longitudinal relative displacement between the detection holder housing 529 and detection holder around 523. In other words, the detection holder 521 is connected to the image detection sensor 510 and the detection holder around 523. The detection holder around 523 is connected to the detection holder housing 529 so as to enable the relative movement therebetween.

As shown in FIG. 13, the detection holder housing 529 is formed in a structure in which it is opened at a bottom surface thereof and is fixedly seated on the radial extending part 131 of the inward receiving body 130. The detection holder 521 and the detection holder around 523 are disposed within the detection holder housing 529. The detection holder 521 is fixed to the end of the image detection sensor 510 which is implemented as an infrared camera, and the detection holder around 523 disposed at the outside of the detection holder 521 is disposed so as to be connected to the detection holder housing 529 so as to enable the relative movement therebetween. In FIG. 13, the image detection sensor 510 and the inward receiving plate 135 are disposed so as to be spaced part from each other. Preferably, the image detection sensor 510 and the inward receiving plate 135 are disposed so as to be in close contact with each other to enable the relative displacement therebetween, if necessary.

Figure 14:
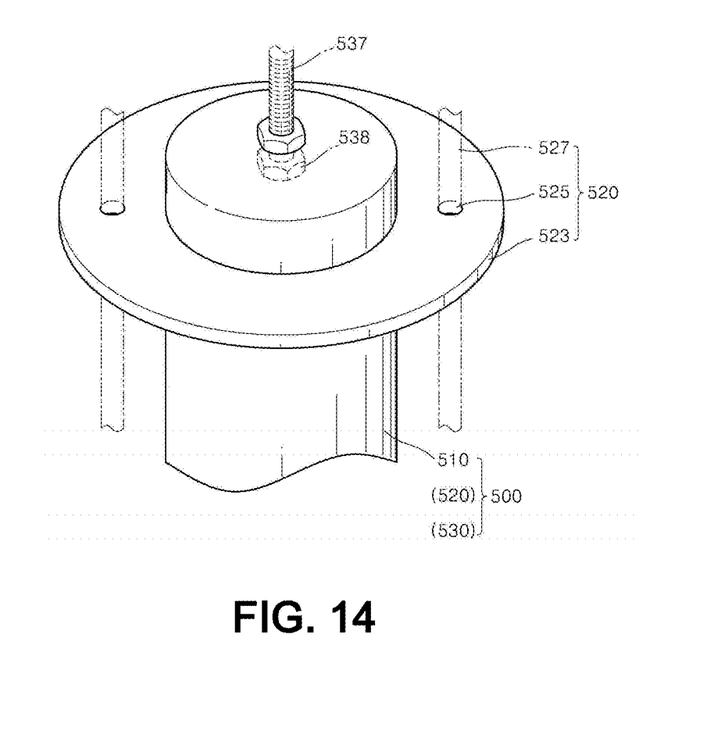
FIG. 14 is a partial perspective view showing an image detection drive unit of a probe station for the simultaneous measurement of thermal and electrical characteristics of a thermoelectric element in accordance with another embodiment of the present invention.

In FIG. 14, there is shown an example of a structure in which the detection holder around 523 and the detection holder housing 529 are connected to each other to enable the relative movement therebetween. The detection holder around 523 includes a through-hole 525 formed therein. The detection holder housing 529 includes a holder housing shaft 527. The holder housing shaft 527 is fixedly mounted at one end thereof to the upper inner surface of the detection holder housing 529 and is fixedly mounted at the other end thereof to one surface of the radial extending part 131 of the inward receiving body 130. The holder housing shaft 527 is disposed penetratingly in the through-hole 525 of the detection holder around 523. Each of the holder housing shaft 527 and the through-hole 525 may be provided in plural numbers, and preferably has a structure in which they are arranged at equal angles from the center of the detection sensor 510. A separate bearing may be provided between the holder housing shaft 527 and the through-hole 525 so as to ensure the stable and smooth relative movement therebetween, if necessary.

As such, the detection holder 521 and the detection holder around 523 have a structure in which they can be movably guided linearly by the holder housing shaft 527 and the through-hole 525 in the detection holder housing 529 to form a vertically movable and stable structure so that the focusing position of the image detection sensor 510 can be adjusted stably.

Figure 15:
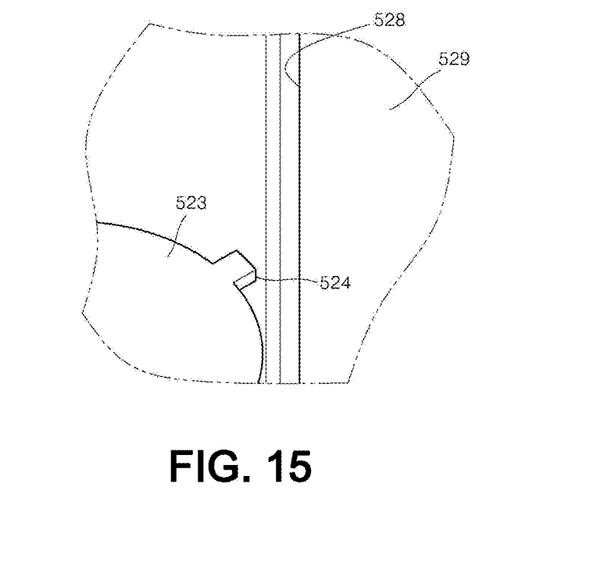
FIG. 15 is a partial perspective view showing an image detection drive unit of a probe station for the simultaneous measurement of thermal and electrical characteristics of a thermoelectric element in accordance with another embodiment of the present invention.

As shown in FIG. 15, the detection holder around 523 includes a holder around guide 524 formed on the outer peripheral surface thereof and the detection holder housing 529 includes a holder housing guide 528 formed on the inner peripheral surface thereof to correspond to the holder around guide 524, if necessary.

The holder around guide 524 is formed as a protruding rib structure in this embodiment, and the holder housing guide 528 is formed as a grooved structure, and vice versa. The holder around guide 524 and the holder housing guide 528 are engaged with each other so that they have a stable holding structure through the guide during the relative movement between the detection holder 521 and the detection holder around 523 in the detection holder housing 529.

In the meantime, the displacement of the detection holder 521 can be performed through the image detection drive unit connected to the detection holder 521. The image detection drive unit may have a structure in which it is disposed at an end thereof on one surface of the detection holder 521 and is passed at the other end thereof through the detection holder housing 529 so as to be exposed to the outside, but the image detection drive unit 530 of the present invention may have an automatic position adjustment structure. In other words, the image detection drive unit 530 includes a detection driver 531, a detection drive transfer unit 533; 535; 537.

The detection driver 531 is implemented as an electric motor and is driven in response to a drive control signal applied thereto from the control unit 20 to generate a driving force for displacing the image detection sensor 510.

The detection drive transfer unit 533; 535; 537 is connected at one end thereof to the detection driver 531 and is connected at the other end thereof to the detection holder 521 to transfer the driving force generated from the detection driver 531 to the detection holder 521. The detection drive transfer unit 533; 535; 537 includes a transfer driving part 533, a transfer driven part 535, and a transfer shaft 537. The transfer driving part 533 is connected to a driving shaft of the detection driver 531, and the transfer shaft 537 is rotatably disposed so as to penetrate through the detection holder housing 529. The transfer shaft 537 is rotatably connected at one end thereof to the detection holder 521 and is disposed at the other end thereof at the outside of the chamber. The transfer shaft 537 includes a transfer shaft holder 538 at one end thereof. The transfer shaft holder 538 is received in the detection holder 521 so as to be freely rotatably moved, and the transfer driven part 535 is disposed on the outer periphery of the transfer shaft 537. In other words, the transfer shaft holder 538 has a hinge connection structure in which it is freely rotatably movable relative to the detection holder 521 in the receiving space of the detection holder 521 so that the transfer shaft holder 538 can be received in one surface of the detection holder 521 and can smoothly transfer a force for allowing for the linear movement thereof to the detection holder 521.

The transfer driven part 535 is connected to the transfer driving part 533 and receives the driving force generated from the detection driver 531 through the transfer driving part 533 to rotate the transfer shaft 537. The transfer shaft 537 has a screw thread formed on the outer peripheral surface thereof so as to be engaged with a screw thread formed on the inner peripheral surface of a through-hole formed in the detection holder housing 529 so that the transfer shaft 537 is linearly moved. A relative rotation between the transfer shaft holder 538 and the detection holder 521 occurs at the end of the transfer shaft 537 and the image detection sensor 510 connected to the detection holder 521 is also linearly moved along with the linear movement of the transfer shaft 537 so that the focusing position of the thermographic image of the element can be adjusted depending on the movement of the image detection sensor 510.

While the present invention has been described in connection with the exemplary embodiments illustrated in the drawings, they are merely illustrative and the invention is not limited to these embodiments. It will be appreciated by a person having an ordinary skill in the art that various equivalent modifications and variations of the embodiments can be made without departing from the spirit and scope of the present invention. Therefore, the true technical scope of the present invention should be defined by the technical spirit of the appended claims.

What is claimed is:

1. A probe station for the simultaneous measurement of thermal and electrical characteristics of a thermoelectric element, comprising:
   a chamber including an inward receiving unit having a window, the inward receiving unit being configured to be seated inwardly of the chamber through a chamber cover opening formed on one surface thereof;
   a base disposed within the chamber;
   a platform disposed on the base and configured to allow the element to be disposed thereon so that a voltage of the element is detected, the platform being configured to allow a platform terminal for detecting a voltage signal of the element to be disposed thereon;
   a probe unit disposed at one end thereof within the chamber and including a probe tip that can be connected to the platform terminal;
   a heat source disposed within the chamber and configured to provide heat to the element so that the voltage signal of the element can be detected; and
   an infrared image detection unit at least partially disposed in the inward receiving unit so that a thermographic image of the element, which is generated by reaction due to heat provided from the heat source, can be acquired through the window, and wherein the thermographic image and the voltage signal of the element are synchronized in real time.

2. The probe station according to claim 1, wherein the window is a Ge window configured to allow an infrared ray to transmit therethrough.

3. The probe station according to claim 1, wherein the platform is disposed on the base and comprises a platform plate for allowing the platform terminal to be disposed thereon, and wherein the platform terminal comprises:
a terminal line configured to form a pair so as to be disposed opposed to each other on one surface of the platform plate, and configured to allow the element to be disposed between the pair of terminal lines; and
a terminal tip disposed at an end of the terminal line and configured to allow the probe tip to be brought into close contact therewith.

4. The probe station for according to claim 3, wherein the heat source is a joule heater disposed on the platform plate, and wherein the heat source comprises:
a heater line disposed at the outside of the terminal line, which is disposed on one surface of the platform plate so that the element can be disposed on the terminal line; and
a heater tip disposed at and end of the heater line and configured to allow an electrical signal to be applied thereto.

5. The probe station according to claim 4, wherein the heat source forms a pair so as to be disposed opposed to each other relative to the center of the terminal line so that heat can be outputted individually.

6. The probe station according to claim 1, further comprising:
a storage unit for storing the thermographic image and the electrical characteristics of the element in response to a storage control signal, and pre-stored temperature reference data that enables a temperature state of the thermographic image to be grasped;
a control unit for in real time, synchronizing the thermographic image and the voltage signal of the element, which are previously stored in the storage unit, and calculating a heat temperature difference occurring at both ends of the element based on the thermographic image and the pre-stored temperature reference data; and
an arithmetic unit for calculating the characteristics of the element in response to an arithmetic control signal from the control unit based on the heat temperature difference and the voltage signal of both ends of the element.

7. The probe station according to claim 1, wherein the inward receiving unit comprises:
an inward receiving body fixedly mounted in the chamber cover opening;
an inward receiving plate disposed spaced apart from the inward receiving body and configured to be movable toward the inside of the chamber, with the window formed in the inward receiving plate; and
an inward receiving bellows connected at one end thereof to the inward receiving body and connected at the other end thereof to the inward receiving plate so that the inward receiving bellows can be folded depending on the position of the inward receiving plate.

8. The probe station according to claim 7, further comprising a receiving unit guide connected at one end thereof to the inward receiving plate through the inward receiving body and disposed at the other end thereof at the outside of the chamber to allow the receiving unit guide to be adjusted in length through the other end of the receiving unit guide so that the inward receiving plate is adjusted in position.

9. The probe station according to claim 1, wherein the image detection unit comprises:
an image detection sensor for acquiring a thermographic image of the element through the window; and
an image detection holding part for allowing the image detection sensor to be maintained at the outside of the chamber.

10. The probe station according to claim 9, wherein the mage detection holding part comprises:
a detection holder disposed so as to be connected to an end of the image detection sensor;
a detection holder around formed extending radially outwardly from an outer circumferential surface of the detection holder; and
a detection holder housing disposed at the outside of the detection holder around to enable the longitudinal relative displacement between the detection holder housing and detection holder around.

11. The probe station according to claim 10, wherein the detection holder around comprises a holder around guide formed on the outer peripheral surface thereof, and
wherein the detection holder housing comprises a holder housing guide formed on the inner peripheral surface thereof so as to be engaged with the holder around guide to enable the relative movement between the holder housing guide and the holder around guide.

12. The probe station according to claim 10, wherein the detection holder around comprises a through-hole formed therein, and
wherein the detection holder housing comprises a holder housing shaft disposed penetratingly in the through-hole of the detection holder around so that the image detection sensor can be moved longitudinally.

13. The probe station according to claim 10, wherein the image detection unit comprises an image detection drive unit configured to drive the image detection holding part to provide a driving force for displacing the image detection sensor to the detection holder, and
wherein the image detection drive unit comprises:
a detection driver for generating the driving force for displacing the image detection sensor; and
a detection drive transfer unit connected at one end thereof to the detection driver and connected at the other end thereof to the detection holder to transfer the driving force generated from the detection driver to the detection holder.

* * * * *